(12) United States Patent
Kenowski et al.

(10) Patent No.: US 12,208,064 B2
(45) Date of Patent: Jan. 28, 2025

(54) POLYURETHANE BONDING SKELETON FOR FEEDING TUBE DEVICE

(71) Applicant: Avent, Inc., Alpharetta, GA (US)

(72) Inventors: Michael A. Kenowski, Alpharetta, GA (US); James M. Takeuchi, Alpharetta, GA (US); Curry B. Sandven, Cumming, GA (US)

(73) Assignee: Avent, Inc., Alpharetta, GA (US)

( * ) Notice: Subject to any disclaimer, the term of this patent is extended or adjusted under 35 U.S.C. 154(b) by 328 days.

(21) Appl. No.: 16/863,506

(22) Filed: Apr. 30, 2020

(65) Prior Publication Data
US 2021/0338533 A1 Nov. 4, 2021

(51) Int. Cl.
*A61J 15/00* (2006.01)
*A61L 29/04* (2006.01)
(Continued)

(52) U.S. Cl.
CPC ....... *A61J 15/0061* (2013.01); *A61J 15/0042* (2013.01); *A61L 29/049* (2013.01); *B29C 45/1459* (2013.01); *B29C 45/1671* (2013.01); *B29K 2069/00* (2013.01); *B29K 2075/00* (2013.01); *B29L 2031/753* (2013.01)

(58) Field of Classification Search
CPC ................ A61J 15/0061; A61J 15/0042; A61J 15/0057; A61J 15/0015; A61J 15/0023; A61J 15/0065; A61J 15/0092; A61J 15/0034; A61J 15/0069; A61L 29/049; A61M 39/0247; A61M 2039/0255; A61M 2039/0261; A61M 2039/267; B29C 45/1671
See application file for complete search history.

(56) References Cited

U.S. PATENT DOCUMENTS 1,755,899 A 4/1930 Root
4,668,225 A 5/1987 Russo et al.
(Continued)

FOREIGN PATENT DOCUMENTS

DE 10 2009 048 584 B3 4/2012
EP 3 429 548 A1 1/2019
WO WO 2017/160308 A1 9/2017

OTHER PUBLICATIONS

International Search Report and Written Opinion for PCT/US2021/029653, dated Aug. 5, 2021, 12 pages.

*Primary Examiner* — Laura A Bouchelle
(74) *Attorney, Agent, or Firm* — Meunier Carlin & Curfman LLC

(57) ABSTRACT

A feeding tube port for use in connection with an enteral feeding system is provided. The feeding tube port includes an inner core made of a first material and an over-layer made of a second material. The over-layer at least partially encloses the inner core, such that the inner core is configured to resist separation from the over-layer. In some aspects, the inner core may be formed from a rigid plastic material and the over-layer may be formed from a pliable material. The inner core may include one or more ribs, slots and/or apertures configured to enhance adherence between the inner core first material and the over-layer second material. The inner core may further include one or more contact points configured for attachment of a feeding tube valve other similar component to the feeding tube port.

20 Claims, 6 Drawing Sheets

(51) Int. Cl.
   *B29C 45/14*   (2006.01)
   *B29C 45/16*   (2006.01)
   *B29K 69/00*   (2006.01)
   *B29K 75/00*   (2006.01)
   *B29L 31/00*   (2006.01)

(56) References Cited

U.S. PATENT DOCUMENTS

| | | |
|---|---|---|
| 4,944,732 A | 7/1990 | Russo |
| 5,082,025 A | 1/1992 | DeVries et al. |
| 5,234,417 A | 8/1993 | Parks et al. |
| 5,322,073 A | 6/1994 | Michels et al. |
| 5,413,561 A | 5/1995 | Fischell et al. |
| 6,375,231 B1 | 4/2002 | Picha et al. |
| 6,464,686 B1 | 10/2002 | O'Hara et al. |
| 8,968,271 B2 | 3/2015 | Guala |
| 10,071,234 B2 | 9/2018 | Koelper et al. |
| 10,426,708 B2 | 10/2019 | Millis et al. |
| 2004/0147874 A1* | 7/2004 | Kliem ............... A61J 15/0042 604/96.01 |
| 2006/0004345 A1 | 1/2006 | McMichael |
| 2006/0027270 A1 | 2/2006 | Truitt et al. |
| 2006/0079850 A1 | 4/2006 | Adams et al. |
| 2006/0195066 A1 | 8/2006 | Cross, Jr. |
| 2010/0292673 A1 | 11/2010 | Korogi et al. |
| 2011/0065319 A1 | 3/2011 | Oster et al. |
| 2011/0230828 A1 | 9/2011 | Shaughnessy et al. |
| 2012/0041425 A1 | 2/2012 | Tsunematsu et al. |
| 2012/0245519 A1* | 9/2012 | Rotella ............... A61J 15/0088 604/99.04 |
| 2014/0207100 A1* | 7/2014 | Webb ............... A61B 17/3462 604/525 |
| 2017/0209656 A1* | 7/2017 | Linton ............... A61M 16/0605 |
| 2017/0367932 A1 | 12/2017 | Millis et al. |
| 2019/0070403 A1 | 3/2019 | Griffith et al. |

* cited by examiner

POLYURETHANE BONDING SKELETON FOR FEEDING TUBE DEVICE

FIELD OF THE INVENTION

The subject matter of the present invention relates generally to a polyurethane bonding skeleton for a feeding tube device such as a gastrostomy feeding tube port.

BACKGROUND

Various medical systems utilize components that are intended to deliver one or more fluids to a patient or other person being treated. One example of such a system is an enteral feeding system in which fluid nutrient formula or the like is delivered via a series of tubing segments to a patient. Certain patients are unable to take food transorally due to an inability to swallow or some other malady associated with the digestive system. Such an inability to swallow may be due to a variety of reasons, such as esophageal cancer, neurological impairment and the like. Although the intravenous administration of food and/or medications to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. Feeding is then typically performed by administering food through a feeding tube that has been inserted into the feeding tract, with the distal end of the feeding tube extending into several locations within the digestive system (stomach, duodenum, jejunum, small intestine, etc.) depending on the particular need(s) of the patient. The feeding tube is retained therein by an internal anchor or bolster and the proximal end of the feeding tube extending through the abdominal wall, and is commonly referred to by the type of access the tube provides to the digestive system, e.g. gastrostomy (G) for stomach access, gastric-jejunal (GJ) for stomach and jejunal access, and jejunal (J) for jejunal access. Feeding tubes are generally offered in two different styles, which differ in the design of the portion of the tube external to the patient. In the first style of tube, a portion of tubing extends beyond the opening of the stoma tract such that the feed head or port is some distance away from the external surface of the patient's abdominal skin. These types of tubes are generally referred to as "standard length" and are typically secured on the proximal end by a movable external bolster. The second style of tube is generally referred as "low-profile" and consists of a feed head or port that rests directly on the patient's abdomen. In this embodiment, the feed head or port also serves as the means to retain the feeding tube from the outside of the patient.

However, the use of such feeding tube devices suffers from its own set of shortcomings. One such shortcoming is that such devices may not last for an extended duration of time, most commonly due to failure of their internal anchoring mechanisms or due to clogging or other failure of their valve mechanisms, and therefore must be replaced frequently. For instance, a typical low-profile gastronomy port may be made from a rigid polycarbonate valve bonded to a soft or pliable port made from, e.g., silicone or polyurethane. However, due to difficulties in bonding dissimilar materials, the rigid polycarbonate may often separate or delaminate from the soft or pliable materials, which can result in leaking or "feeding the bed" and preventing a patient from receiving food through the gastronomy device. Moreover, securing components after molding of a pliable material such as silicone or polyurethane is very difficult because, in many cases, the bonding between materials does not fail until after hundreds or even thousands of cycles in use.

Consequently, there is a need for a feeding tube device and method of manufacturing thereof having improved bonding between components having dissimilar materials.

SUMMARY

Objects and advantages of the invention will be set forth in part in the following description, or may be obvious from the description, or may be learned through practice of the invention.

The present invention is directed to a feeding tube port for use in connection with an enteral feeding system. The feeding tube port includes an inner core made of a first material and an over-layer made of a second material. The over-layer at least partially encloses the inner core. The inner core is configured to resist separation from the over-layer.

In one particular embodiment, the first material can be a rigid plastic material.

In one embodiment, the second material can be a pliable material.

In one embodiment, the inner core can include one or more ribs, slots and/or apertures configured to enhance adherence between the inner core first material and the over-layer second material.

In one embodiment, the feeding tube can include an inner lumen extending through the inner core and the over-layer.

In one embodiment, the inner core can include one or more contact points configured for attachment of a feeding tube component to the feeding tube. Further, the one or more contact points can include at least one snap, twist, or locking feature for attaching the feeding tube component to the feeding tube.

In one embodiment, the inner core can include a surface comprising printed or molded text that is configured to be visible through the over-layer.

In one embodiment, the first material can be a rigid thermoplastic.

In one embodiment, the second material can be a thermoplastic elastomer.

In one embodiment, the feeding tube port can further include a feeding port and a balloon port, wherein the feeding port is formed by the inner core and the over-layer. Further, the balloon port can be formed by the inner core and the over-layer.

In one embodiment, the inner core can be a unitary structure.

In one embodiment, the first material can be polycarbonate and the second material can be polyurethane.

In one embodiment, the inner core can have a generally cylindrical shape. Further, the inner core can include one or more ribs, slots and/or apertures in an upper surface, lower surface, or side surface of the cylindrical shape.

The present invention is further directed to a method of manufacturing feeding tube port for use in connection with an enteral feeding system. The method includes steps of: molding an inner core made of a first material, wherein the inner core comprises an upper surface, a lower surface and a side surface; and overmolding an over-layer made of a second material such that the over-layer at least partially encloses the inner core, wherein the inner core is configured to resist separation from the over-layer.

In one particular embodiment of the method, the inner core can include one or more ribs, slots and/or apertures in the upper surface, the lower surface, or the side surface, further wherein the step of overmolding the over-layer can include filling in voids created by the ribs, slots and/or apertures in the inner core with the second material of the over-layer.

In one embodiment, the first material can be polycarbonate and the second material can be polyurethane.

In one embodiment, the steps of molding the inner core and overmolding the over-layer over the inner core can be integrated steps of a single manufacturing process.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
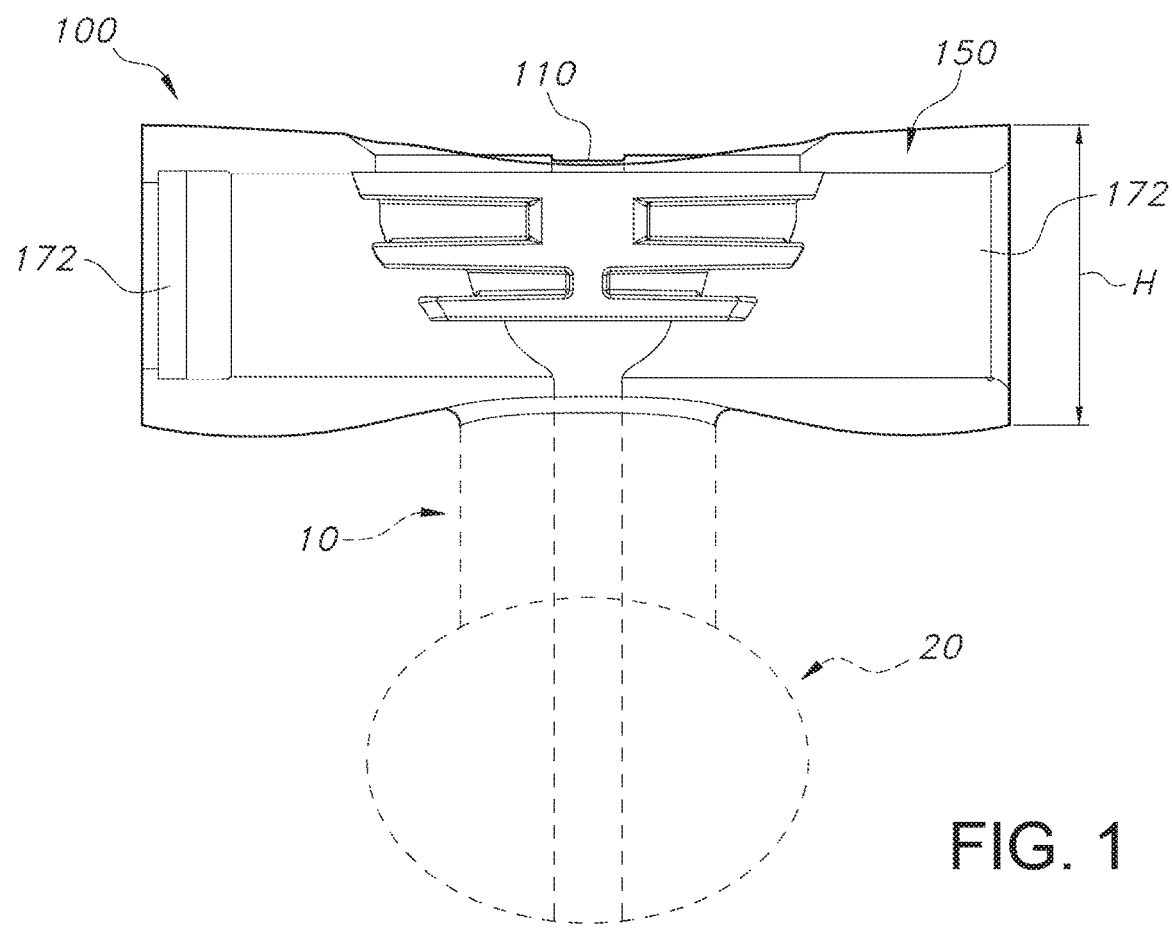
FIG. 1 illustrates a side view of a feeding tube port having an inner core and an over-layer according to one particular embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to a feeding tube port for use in connection with an enteral feeding system. The feeding tube port includes an inner core made of a first material and an over-layer made of a second material. The over-layer at least partially encloses the inner core, such that the inner core is configured to resist separation from the over-layer. In some aspects, the inner core may be formed from a rigid plastic material and the over-layer may be formed from a pliable material. The inner core may include one or more ribs, slots and/or apertures configured to enhance adherence between the inner core first material and the over-layer second material. The inner core may further include one or more contact points configured for attachment of a feeding tube valve to the feeding tube port. The present inventors have found that the formation of the feeding tube port from a rigid inner core and a pliable over-layer having mechanical bonding between the inner core and the over-layer enhances adherence between the inner core and the over-layer. When the inner core provides additional contact points for components that are made from a similar material as the inner core such as a feeding tube valve, the inner core acts as an anchor for such other components, thereby reducing the likelihood of delamination or detachment between the feeding tube valve and the pliable port. The specific features of the feeding tube port of the present invention may be better understood with reference to FIGS. 1-11.

Figure 2:
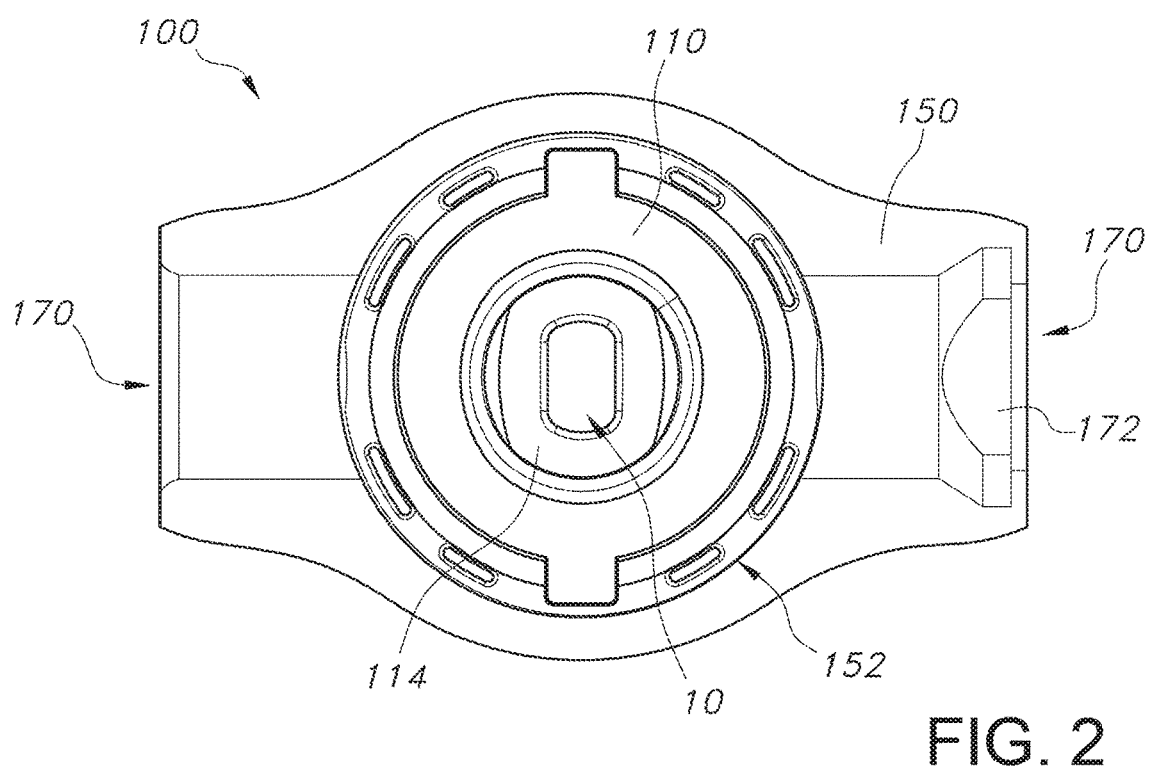
FIG. 2 illustrates a top view of the feeding tube port of FIG. 1.

FIGS. 1 and 2 illustrate one or more embodiments of a feeding tube port 100 of the present invention. For instance, the feeding tube port 100 may be a low-profile gastrointestinal feeding tube port for use with an enteral or gastrointestinal feeding system. The feeding tube port 100 includes an inner core 110 and an over-layer 150 that at least partially encloses the inner core 110. The feeding tube port 100 is connected to a feeding tube 10. For instance, the inner core 110 may include an aperture 114 and the over-layer 150 may include an opening 156 which are aligned and configured to be in communication with the feeding tube 10. The over-layer 150 includes an over-molded portion 152 defined by the surface area of contact between the inner core 110 and the over-layer 150.

As best shown in FIGS. 1-2 and 4-5, the inner core 110 defines the internal skeleton of the feeding tube port 100. The inner core 110 is made from a first material that is more rigid than the material of the over-layer 150. In some aspects, the inner core 110 may be formed as a unitary structure, i.e., manufactured, e.g., by molding, as a single unitary piece. The inner core 110 has an upper surface 112, a lower surface 118, and a side surface 116 extending between the upper surface 112 and the lower surface 118. Additionally, the inner core 110 can include an aperture 114 extending therethrough from the upper surface 112 to the lower surface 118. The aperture 114 can provide a channel or lumen for delivering food or other fluid through the feeding tube port 100 to the patient. The aperture 114 can also provide a channel or lumen for extracting fluids through the feeding tube port 100 from the patient, as is the case in instances such as gastric decompression. The upper surface 112 may further include a valve seat 130, shown as a round or generally circular indentation in the upper surface 112 in FIG. 2, in which a valve 200 or other component can be seated as will described in more detail below. The upper surface 112 may also include one or more contact points 132 at which the upper surface 112 can receive and retain the valve 200 or other component(s) to be attached to the upper surface 112 of the inner core 110. The contact points 132 may include one or more of a snap, twist, or locking feature for securely attaching the valve 200 or other component(s) to the inner core 110. As shown in FIG. 2, the upper surface 112 of the inner core 110 may be exposed. However, the present inventors also contemplate configurations in which at least a portion of the upper surface 112 is encapsulated by the over-molded portion 152 of the over-layer 150.

In some embodiments, the inner core 110 can have a generally cylindrical shape having a diameter that is generally larger than the height H. For instance, the inner core 110 can have a generally circular shaped upper surface 112 having a diameter D1. The lower surface 118 may also have a generally circular shape having a diameter D2 that is approximately equal to the diameter D1. Additionally, the aperture 114 through the inner core 110 has a diameter D4 that is smaller than the diameter D1 and D2 of the upper surface 112 and lower surface 118, respectively.

Figure 4:
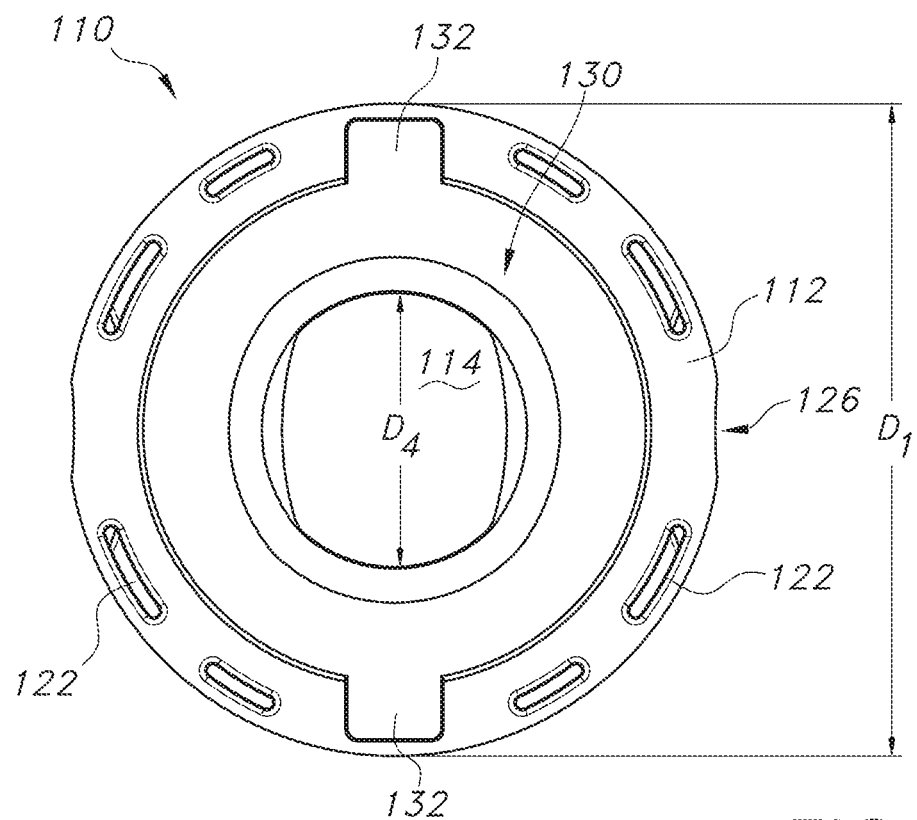
FIG. 4 illustrates a top view of the inner core of the feeding tube port of FIG. 1.
Figure 5:
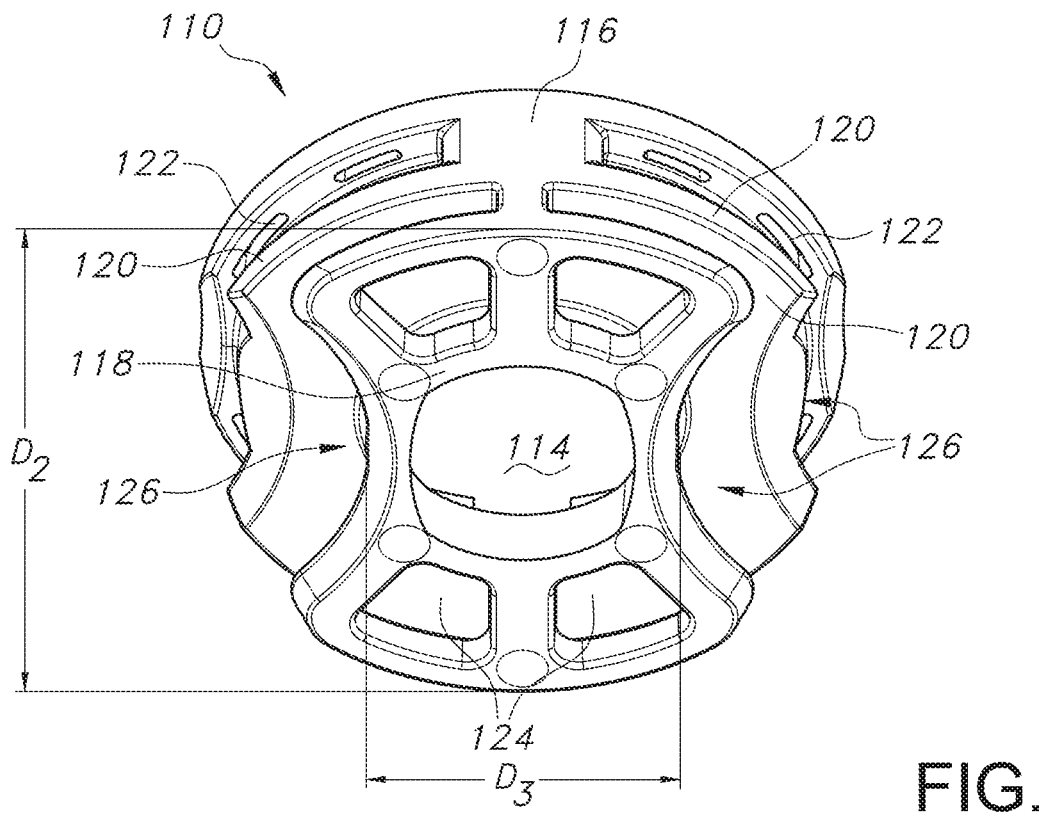
FIG. 5 illustrates a perspective view of the inner core shown in FIG. 4.

Portions of the inner core 110, such as the lower surface 118, may further include one or more structures which are configured to prevent separation between the inner core 110 and the over-layer 150. For instance, the inner core 110 includes one or more ribs 120, slots 122, holes/openings 124, and/or cut-outs 126 that increase the surface area for contact between the inner core 110 and the over-layer 150. The ribs 120, slots 122, openings 124 and/or cut-outs or indented portions 126 may be formed in or on the side surface 116, the lower surface 118 and/or the upper surface 112 of the inner core 110. For instance, as shown in FIG. 4, the upper surface 112 may include one or more slots 122 formed in the upper surface 112. Additionally, as shown in FIG. 4, the upper surface 112 may include one or more cut-out or indented portions 126 around the perimeter of the upper surface 112. Further, the side surface 116 of the inner core 110 shown in FIG. 4 can include one or more ribs 120 interposed with slots 122 in between the ribs 120. Additionally, the lower surface 118 of the inner core 110 shown in FIG. 4 can include one or more holes or openings 124 through the lower surface 118 into the adjacent slots 122. The lower surface 118 may also include one or more cut-out or indented portions 126 along the perimeter of the lower surface 118. The lower surface 118 may have a diameter D3 extending across the cut-out or indented portions 126 that is smaller than the diameter D2 of the lower surface 118 yet larger than the diameter D4 of the aperture 114 through the inner core 110. However, any arrangement or combination of ribs 120, slots 122, holes/openings 124 and/or cut-out or indented portions 126 may be formed in the inner core 110 as contemplated by the present invention. The one or more ribs 120, slots 122, holes/openings 124, and/or cut-outs or indented portions 126 provide openings or voids through which the material of the over-layer 150 can fill in to form the over-molded portion 152 so that the inner core 110 is mechanically bonded in place within the over-layer 150.

Additionally, the inner core 110 can have a smooth surface texture and/or a rough, uneven textured surface. For instance, at least a portion of the inner core 110 can have a textured surface having ridges, dimples, rounded protrusions such as hemispheres, pyramids, or any other three-dimensional texture in or on the surface of the inner core 110. By providing a three-dimensional surface texture on the inner core 110, the bonding surface area of the inner core 110 is expanded compared to a smooth surface texture in order to provide increased area for bonding between the over-layer 150 and the inner core 110. The over-layer 150 can fill in voids within the textured surface of the inner core 110 in order to further increase the surface area of the overmolded portion 152 to bond the inner core 110 in place with the over-layer 150.

Figure 3:
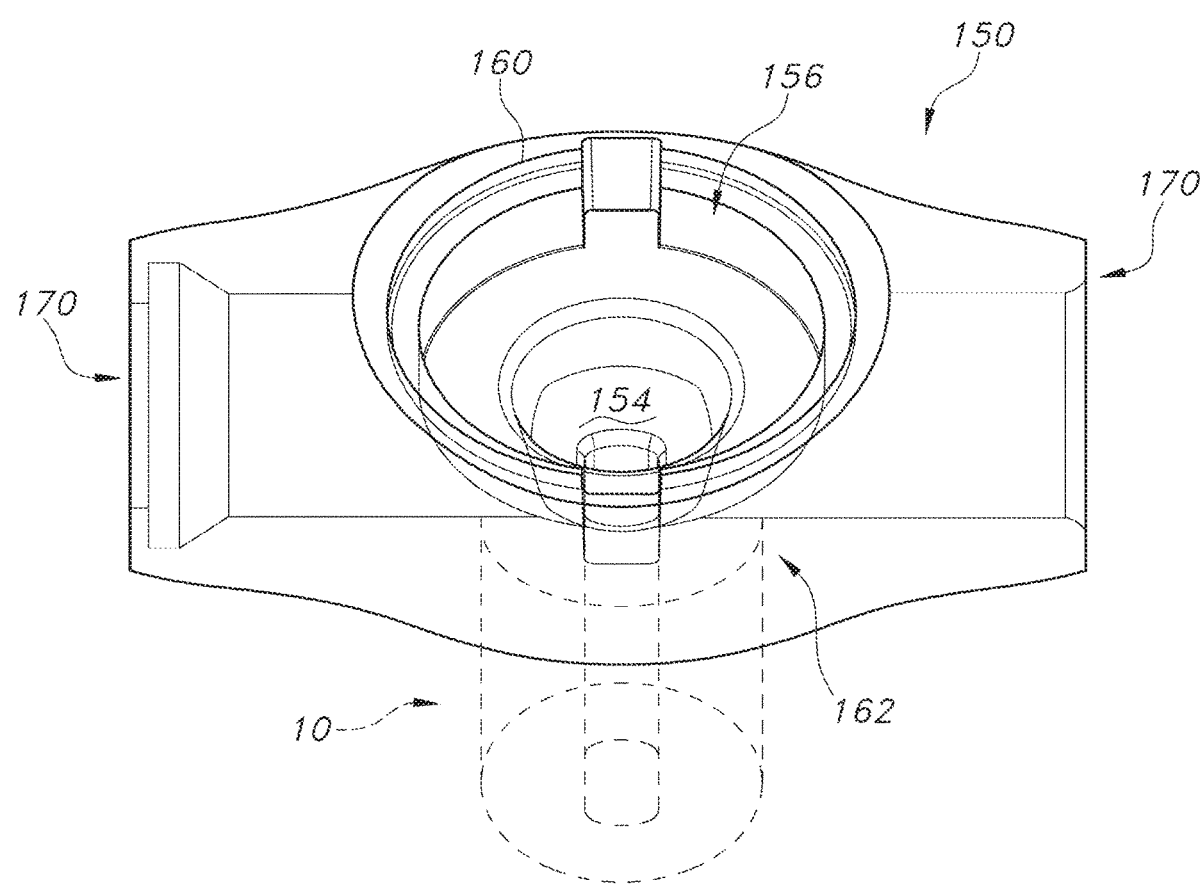
FIG. 3 illustrates a perspective view of the over-layer of the feeding tube port of FIG. 1.

The over-layer 150 forms the outer structure of the feeding tube port 150 as shown in FIGS. 1-3. The over-layer 150 is made of a second, pliable material such as a thermoplastic elastomer in some embodiments. When such an elastomer is used, it can be a medical-compliant over-mold that adheres to various substrates, including the types of more rigid material used in the inner core 110, noted above. This type of material has a rubber feel and soft touch and is typically clear or translucent. For instance, the second material can be used in injection molding fabrication, as will be discussed in greater detail. Over-layer 150 also can be made of an opaque material, including materials that can possess preselected color characteristics. Over-layer 150 provides a good gripping material for individuals who are handling and manipulating the feed valve port 100 (e.g., nurse, clinician, caregiver, patient, etc.) and also provides a resilient enclosure that permits the use of a more rigid first material for the inner core 110 while protecting the inner core 110 from breakage, damage, slipperiness and other undesirable characteristics. Moreover, the soft, flexible material of over-layer 150 allows the feed valve port 100 to be comfortably placed in close proximity to a patient's exposed skin. The combination of the inner core 110 and the over-layer 150 permits an organic, smooth shape that allows for ergonomic gripping of the feed valve port 100 during use and reduces discomfort between the port 100 and the patient's skin.

In one aspect of the present invention, the inner core 110 can be made of polycarbonate and the over-layer 150 can be made of polyurethane. Polyurethane generally has better abrasion and tear resistance than rubber materials, and additionally a higher load bearing capacity, making it a suitable choice of material for the over-layer 150 of the present invention. Polyurethane is also more resistant to many oils, solvents, and weak acids/bases than rubbers. Moreover, polyurethane is a lubricious material, i.e., it seeps lubricant over time. However, these same beneficial characteristics can make polyurethane a difficult material to adhere or bond components that are made from other materials. Thus, over-molding polyurethane over or around a component, such as the inner core 110, is often a preferred method to bond the components together, in addition to using one or more adhesives and/or solvents to bond the components. The present inventors have found that polycarbonate is a material that adheres well to polyurethane, especially when the polyurethane material is overmolded onto a polycarbonate skeleton. Thus, when the inner core 110 is made of polycarbonate and the over-layer 150 made of polyurethane is molded over the inner core 110, desirable bonding characteristics are achieved.

Moreover, as described above, the surface features of the inner core 110 such as the ribs 120, slots 122, openings 124 and/or cut-outs or indented portions 126 increase the surface area of the inner core 110 that can be overmolded with the over-layer 150 to form a greater over-molded portion 152. By enabling the polyurethane to fill in the slots 122, apertures 124 and/or cut-out or indented portions 126 while the ribs 120 stick out or protrude from the inner core 110, the inner core 110 and the over-layer 150 are effectively stitched together by the polyurethane overmolded portion 152. Thus, the inner core 110 can be retained within the over-layer 150 without requiring the use of other adhesive and/or solvent bonding. Instead, the over-molding of the over-layer 150 over the inner core 110 may replace the need for adhesive or solvent bonding between the pliable material(s) and rigid material(s) of the feeding tube port. However, adhesive and/or solvent bonding may be used in addition to the overmolding of the inner core 110 and the over-layer 150. For instance, as will be described in greater detail below, adhesive bonding and/or solvent bonding may be used to bond one or more additional components to the inner core 110 in order to form the feeding tube port 100.

The over-layer 150 is formed by over-molding a pliable material, e.g., polyurethane, around the inner core 110. The over-layer 150 includes a recess 156 for holding or receiving the inner core 110 within the over-layer 150. The recess 156 extends through the over-layer 150 from an upper surface 160 to a lower surface 162. The over-layer 150 is configured to receive a feeding tube 10 within an opening 154 at the lower surface 162. The opening 154 for the feeding tube 10 is in fluid communication with the opening 156 for the inner core 110, and particularly, the opening 154 is in fluid communication with the aperture 114 of the inner core 110 for allowing fluid to pass through the feeding tube port 100 into the feeding tube 10. Moreover, the over-layer 150 can have a rounded, e.g., generally circular, oval or elliptical, shape surrounding the inner core 110 and generally conforming to the outer shape of the inner core 110.

In some aspects, the over-layer 150 of the port 100 can include one or more side ports 170, as shown in FIGS. 1-3 and 9-11. Each side port 170 may include an opening 172 facing generally perpendicular to the opening 156 and feeding tube 10. Each of the side ports 170 can accommodate one or more components that are part of or can be used in conjunction with the feeding tube port 100. For instance, one of the side ports 170 may form a balloon port or other similar port intended to access the feeding tube's internal retention bolster. The balloon port is configured to allow fluid, e.g., air, water, saline, etc., into the balloon 20 of the port 100. The balloon 20 is disposed surrounding the feeding tube 10 and configured to hold the feeding tube 10 in place relative to the patient's body. Thus, after the feeding tube 10 is inserted into the patient's body, the balloon 20 can be inflated via the balloon port 170.

The inner core 110 can be formed, e.g., by a molding process or an extrusion process. For instance, the inner core 110 can be formed by injection molding. The inner core 110 may be manufactured independently prior to over-molding the over-layer 150 onto the inner core 110. In one aspect of the present invention, the inner core 110 can be molded as an integrated step of a single manufacturing process in which the inner core 110 is molded and then the over-layer 150 is overmolded onto the inner core 110, for instance, by injection molding. When the over-layer 150 is overmolded onto the inner core 110, one or more portions of the inner core 110 may be blocked so that they remain free of the over-layer 150. For instance, the upper surface 112 of the inner core 110 may be covered or blocked during the fabrication of the over-layer 150 so that the valve seat 130 and the aperture 114 remain exposed and are not covered by the over-layer 150.

In some aspects, the inner core 110 and/or the over-layer 150 may each have pre-selected color characteristics. For instance, the inner core 110 may have an opaque color such that the inner core 110 can be easily visible or identifiable within the over-layer 150 when the over-layer 150 is clear or translucent. In such an embodiment, the contact points 132 or other component attachments of the inner core 110 may be more easily identifiable when the feeding tube port 100 is observed. Additionally, the inner core 110 can include printed and/or molded text on the upper surface 112, side surface 116 or lower surface 118 that is configured to be visible through the over-layer 150 when the over-layer is clear or translucent. The over-layer 150 may also have an opaque material having preselected color characteristics. For instance, the inner core 110 may have a first color and the over-layer may be formed from at least a second color that is different from the first color. Optionally, the first color and/or second color may be selected to match a color of a subcomponent configured to be bonded with the inner core 110 and/or over-layer 150 in order to enable a user to easily match the colors for properly aligning and attaching the subcomponents. For instance, the balloon port 170 of the over-layer 150 may be formed from a particular color, and an attached balloon valve may be formed from a matching color.

Figure 6:
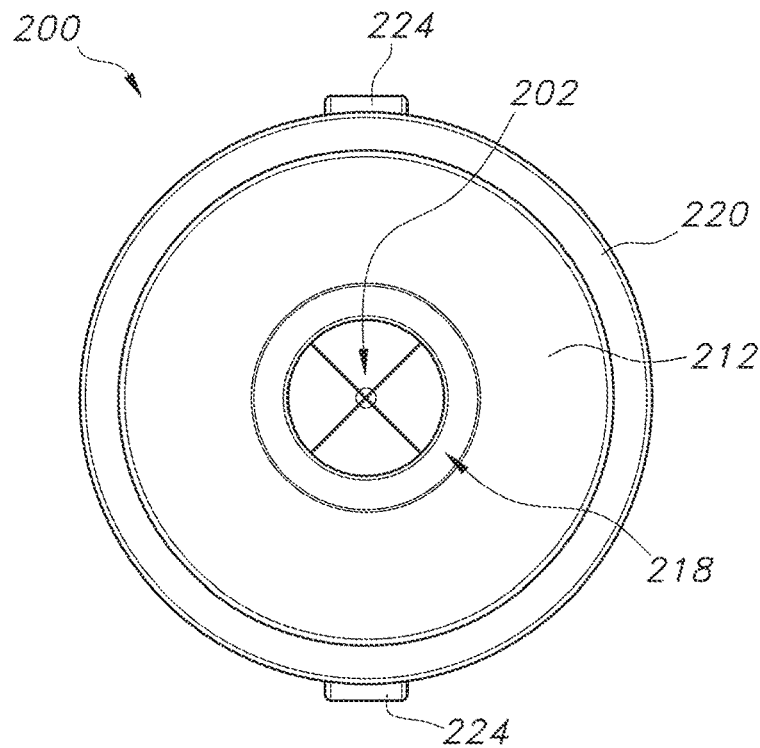
FIG. 6 illustrates a top view of a feeding tube valve configured for attachment with the feeding tube port of FIG. 1.
Figure 7:
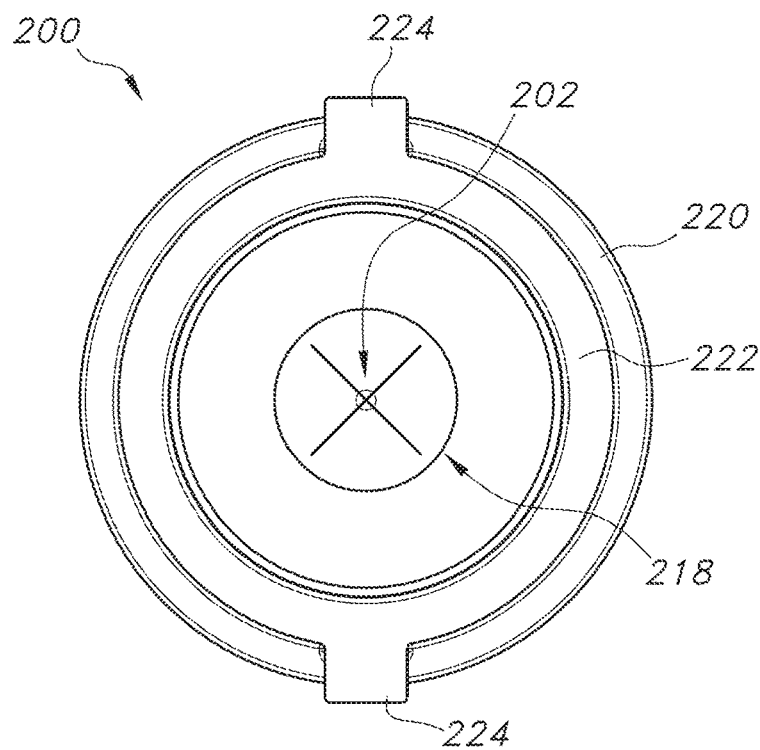
FIG. 7 illustrates a bottom view of the feeding tube valve of FIG. 6.
Figure 8:
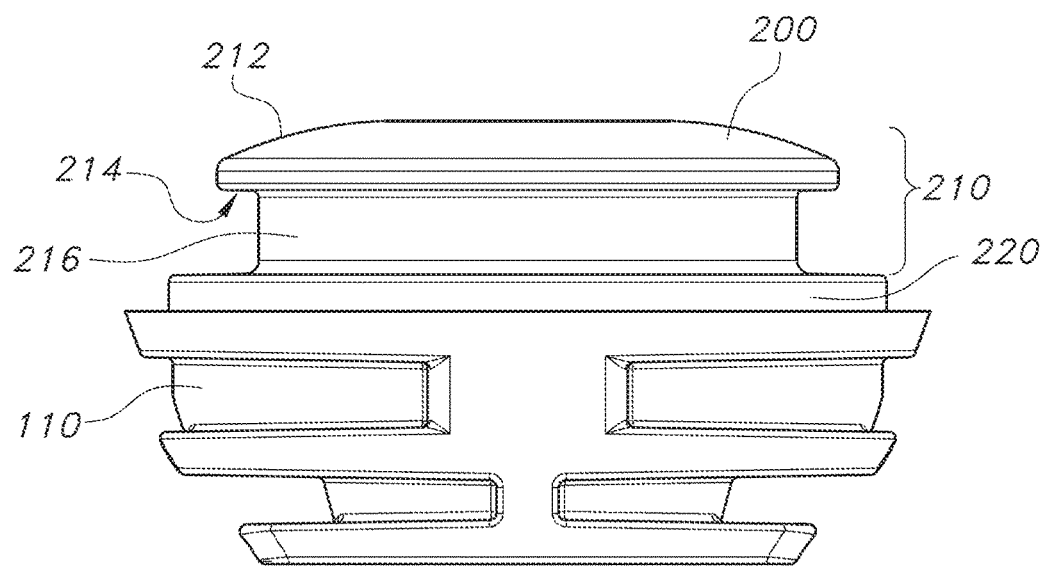
FIG. 8 illustrates a side view of the feeding tube valve of FIGS. 6-7 attached to the inner core of FIGS. 4-5.

As illustrated in FIGS. 6-8, one of the additional components of the feeding tube port 100 may further include a feeding tube valve 200. The feeding tube valve 200 includes an aperture 218 extending therethrough from an upper surface 212 to a lower surface 222. A valve 202 is seated within the aperture 218. The valve 202 may be, for instance, a one-way valve or a two-way valve. For instance, the valve 202 may be formed of an elastomeric material having one or more flaps for opening and closing the valve. As shown in FIG. 6, the valve 202 may include one or more slits within the elastomeric material to form the flaps, such as four flaps formed from a cross-shaped slit illustrated in FIGS. 6 and 7.

The feeding tube valve 200 may also contain a connection portion 210 that may be configured to connect the feeding tube valve 200 with a tube, connector, port or other source of enteral feeding, fluid, medicine, or other substance to be delivered through the feeding tube port 100. The connection portion 210 includes an upper surface 212 which forms an upper surface of the valve 200. The connection portion 210 further includes an inner lip 214 sitting beneath the upper surface 212 and an inner cylinder 216 sitting below the upper surface 212 such that the upper surface 210 sits generally on the inner cylinder 210. Such configuration enables a connector, tube or port that is configured to interface with the connection portion 210 to surround the upper surface 212 and interface with the inner lip 214 formed around the inner cylinder 216.

Figure 9:
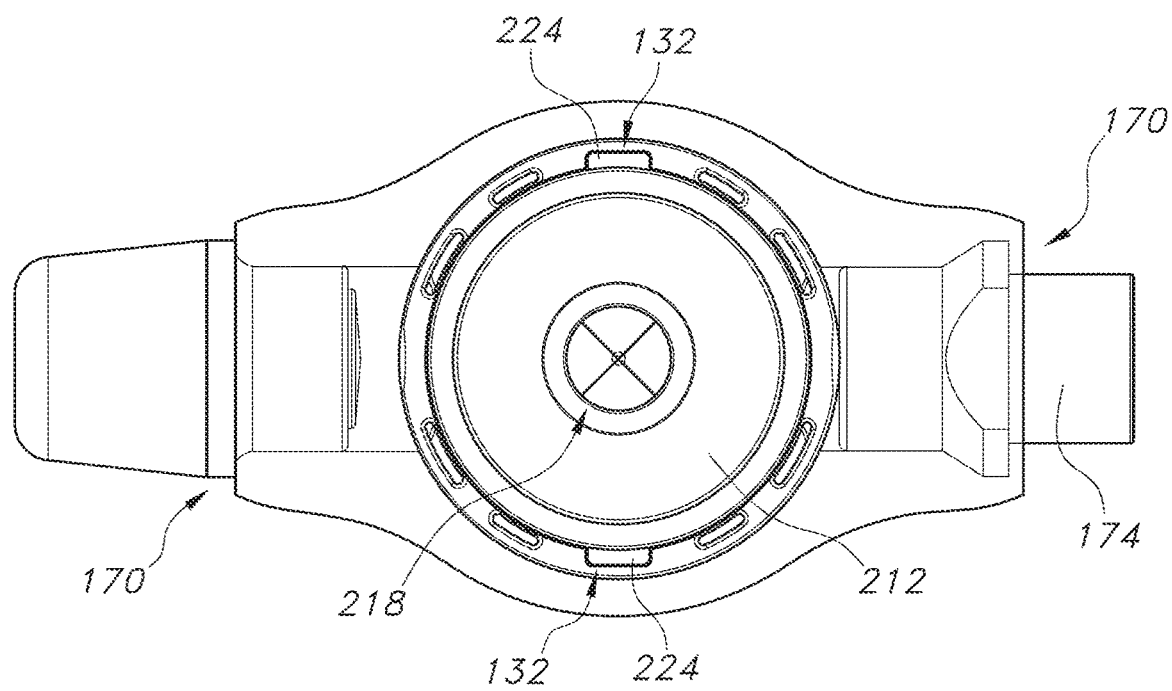
FIG. 9 illustrates a top view of a feeding tube port assembly including the feeding tube port of FIG. 1 and the valve of FIGS. 6-7, in which the feeding tube port assembly includes one or more balloon ports.
Figure 10:
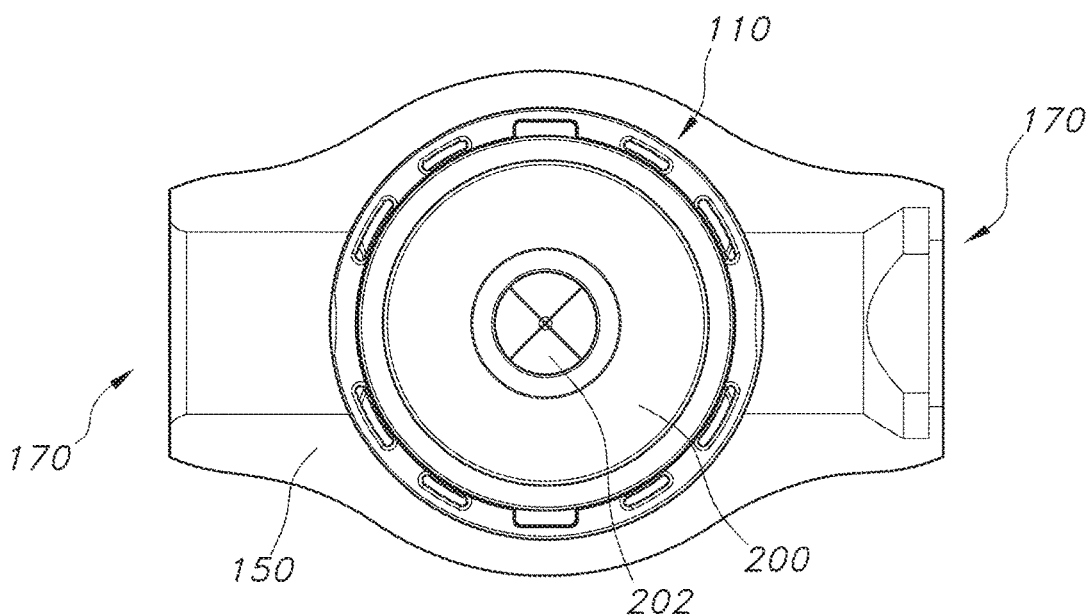
FIG. 10 illustrates a top view of a feeding tube port assembly including the feeding tube port of FIG. 1 and the valve of FIGS. 6-7.
Figure 11:
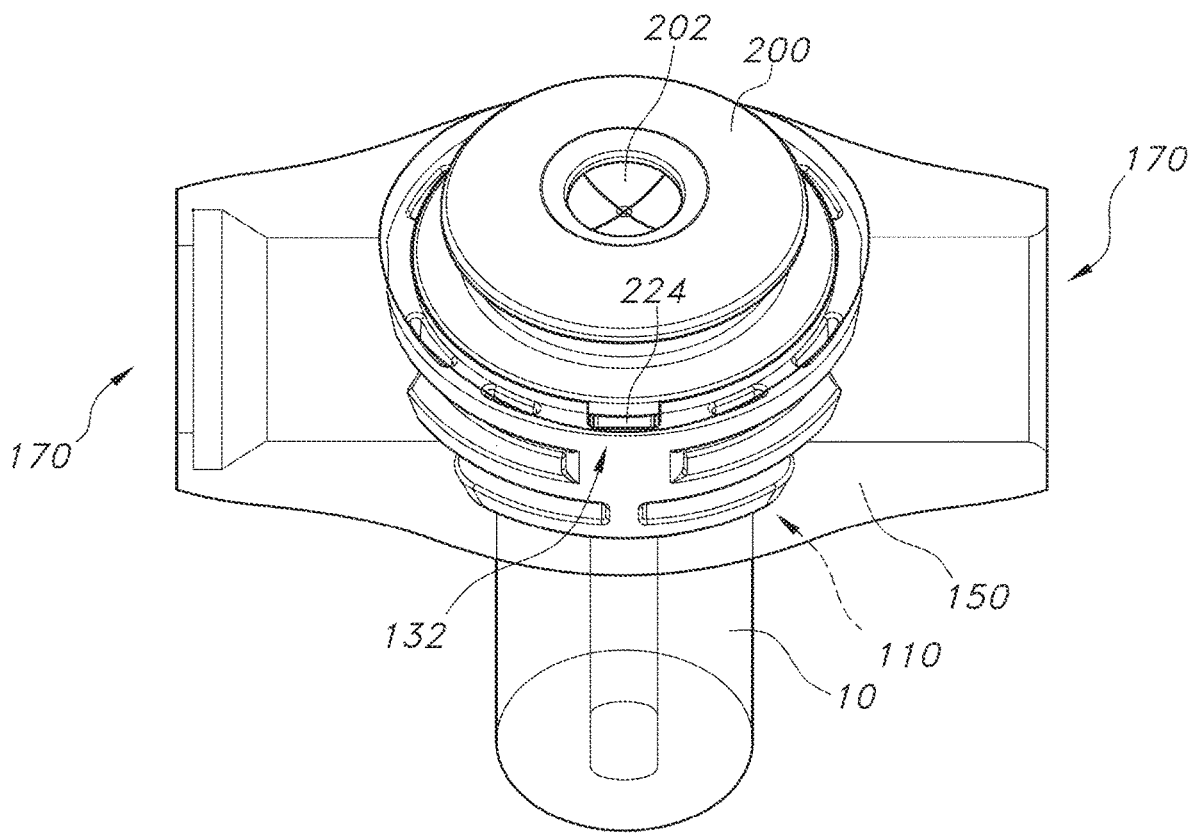
FIG. 11 illustrates a perspective view of a feeding tube port assembly of FIG. 10.

As illustrated in FIGS. 8-9 and 11, the feeding tube valve 200 is configured to fit within the valve seat 130 of the inner core 110 using the attachment portion 220 of the valve 200. The attachment portion 220 can include a seat 222 configured to fit within the valve seat 130 of the inner core 110, and one or more contact points 224 configured to engage with the contact points 132 of the inner core 110. By placing the seat 222 of the in feeding tube valve 200 within the valve seat 130 of the inner core and aligning the contact points 224 with the contact points 132 of the inner core 110, the feeding tube valve 200 can be securely fit and held in place within the inner core 110. In addition to mechanically fitting the feeding tube valve 200 with the inner core 110, the feeding tube valve 200 can be bonded to the inner core 110 such as by an adhesive or solvent bonding. For instance, the bonding between the inner core 110 and the feeding tube valve 200 can use an adhesive such as cyanoacrylate, an ultravioletcured adhesive, a solvent such as dimethyl chlorine, or any other adhesive or solvent suitable for bonding the materials of the inner core 110 and the feeding tube valve 200. In some aspects, the inner core 110 and the feeding tube valve 200 may be made from the same or similar materials. When the inner core 110 and feeding tube valve are formed from the same or similar materials, they may bond together easily. For instance, when both the inner core 110 and the feeding tube valve 200 are formed from polycarbonate, cyanoacrylate adhesive or dimethyl chloride solvent may be used to bond the inner core 110 and feeding tube valve 200 components together.

In addition to or supplemented with adhesive or solvent bonding, the feeding tube valve 200 can also be connected to the inner core 110 via a variety of mechanical attachments. Examples of these types of mechanical attachments include features such as ribs, slots, and other general protrusions that create physical interference between the two components. Additionally, helical features, or the like, may be incorporated into inner core 110 such that the tube valve 200 is assembled and retained via a "twist and lock" type of feature.

As mentioned above, the feeding tube port 100 may additionally include one or more side ports, such as two side ports 170 as shown in FIGS. 1-2 and 9-11. For instance, one of the side ports may be a balloon port for filling an inflatable balloon 20 configured to hold the feeding tube 10 in place. When the balloon 20 is inflated, it serves to hold the feeding tube port 100 and feeding tube 10 in place and prevent leakage of gastric contents via the patient's stoma.

In additional embodiments (not shown), the inner core 110 is configured to form an inner skeleton for a feeding tube port 100 that defines not only the skeleton for the feeding tube valve 200 but also the balloon port 170 and/or any other side port or valve. For instance, the shape of the inner core 110 may include one or more side openings oriented at an angle to the axis of the aperture 114, e.g., generally perpendicular to the axis of the aperture 114, in order to form a skeleton for the balloon port 170. Similarly, the present inventors contemplate the formation of a dual port such as a gastric-jejunal feeding port formed having an inner core and an overmolded layer as described by the present invention. Moreover, any other catheter or port configured to sit in contact with the patient's skin, such as an intravenous line, chemotherapy drug delivery port, ostomy port or stoma, or other suitable medical device port.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A feeding tube port for use in connection with an enteral feeding system, the feeding tube port comprising:
   an inner core made of a first material and an over-layer made of a second material, wherein the over-layer at least partially encloses the inner core,
   wherein the inner core is configured to resist separation from the over-layer,
   wherein the inner core comprises:
      an upper surface, a lower surface, a side surface, and an aperture extending therethrough from the upper surface to the lower surface;
      one or more openings in the upper surface of the inner core located radially outward from the aperture;
      a plurality of openings in the lower surface of the inner core located radially outward from the aperture;
      a first rib extending radially from the side surface of the inner core and circumferentially around the side surface of the inner core and forming a recessed channel extending circumferentially around the inner core between a top surface of the first rib and the upper surface of the inner core.

2. The feeding tube port of claim 1, wherein the first material is a rigid plastic material.

3. The feeding tube port of claim 1, wherein the second material is a pliable material.

4. The feeding tube port of claim 1, wherein the inner core further comprises one or more slots and/or indented portions configured to enhance adherence between the inner core first material and the over-layer second material.

5. The feeding tube port of claim 1, wherein the feeding tube port comprises an inner lumen extending through the inner core and the over-layer.

6. The feeding tube port of claim 1, wherein the inner core comprises one or more contact points configured for attachment of a feeding tube component to the feeding tube port.

7. The feeding tube port of claim 6, wherein the one or more contact points comprises at least one snap, twist, or locking feature for attaching the feeding tube component to the feeding tube.

8. The feeding tube port of claim 1, wherein the inner core comprises a surface comprising printed or molded text that is configured to be visible through the over-layer.

9. The feeding tube port of claim 1, wherein the first material is a rigid thermoplastic.

10. The feeding tube port of claim 1, wherein the second material is a thermoplastic elastomer.

11. The feeding tube port of claim 1, further comprising a feeding port and a balloon port, wherein the feeding port is formed by the inner core and the over-layer.

12. The feeding tube port of claim 11, wherein the balloon port is formed by the inner core and the over-layer.

13. The feeding tube port of claim 1, wherein the inner core is a unitary structure.

14. The feeding tube port of claim 1, wherein the first material is polycarbonate and the second material is polyurethane.

15. The feeding tube port of claim 1, wherein the inner core has a generally cylindrical shape.

16. The feeding tube port of claim 15, wherein the first rib is formed in the cylindrical shape.

17. The feeding tube port of claim 1, wherein the lower surface of the inner core has one or more cut-out or indented portions.

18. The feeding tube port of claim 17, wherein the lower surface of the inner core has a maximum diameter D2 and a diameter D3 across at least one of the one or more cut-out or indented portions, the diameter D3 being less than the diameter D2.

19. The feeding tube port of claim 1, wherein the upper surface of the inner core has a maximum diameter D1, the lower surface of the inner core has a maximum diameter D2, and the diameter D2 is approximately equal to the diameter D1.

20. The feeding tube port of claim 1, wherein the inner core further comprises:

a first shoulder defined between an upper surface of the recessed channel and a first portion of the side surface, the first portion of the side surface extending between the first shoulder and the upper surface of the inner core;

a second shoulder defined between a lower surface of the recessed channel and a second portion of the side surface;

a second rib extending radially from the side surface of the inner core, the second rib spaced axially from the first rib and located between the first rib and a bottom surface of the inner core;

a second recessed channel extending circumferentially around the inner core between a bottom surface of the rib and an upper surface of the second rib.

* * * * *